(12) United States Patent
Copeland et al.

(10) Patent No.: US 6,426,423 B1
(45) Date of Patent: Jul. 30, 2002

(54) METHODS FOR TREATING PHOSPHATIDE-CONTAINING MIXTURES

(75) Inventors: Dick Copeland; W. Maurice Belcher, both of Omaha, NE (US)

(73) Assignee: I.P. Holdings, Omaha, NE (US)

( * ) Notice: Subject to any disclaimer, the term of this patent is extended or adjusted under 35 U.S.C. 154(b) by 0 days.

(21) Appl. No.: 09/776,126

(22) Filed: Feb. 2, 2001

Related U.S. Application Data

(60) Continuation-in-part of application No. 09/550,375, filed on Apr. 14, 2000, now abandoned, which is a division of application No. 09/197,953, filed on Nov. 20, 1998, now Pat. No. 6,172,248.

(51) Int. Cl.[7] ................................. C11B 3/00
(52) U.S. Cl. ................... 554/179; 554/198; 554/212
(58) Field of Search ................. 554/179, 198, 554/212

(56) References Cited

U.S. PATENT DOCUMENTS

| | | |
|---|---|---|
| 2,410,926 A | 11/1946 | Bush et al. |
| 4,036,865 A | 7/1977 | Hartmann et al. |
| 4,049,686 A | 9/1977 | Ringers et al. |
| 4,072,482 A | 2/1978 | Aoki et al. |
| 4,240,972 A | 12/1980 | Mag et al. |
| 4,698,185 A | 10/1987 | Dijkstra et al. |
| 4,713,155 A | 12/1987 | Arutjunian et al. |
| 4,996,072 A | 2/1991 | Marschner et al. |
| 5,696,278 A | 12/1997 | Segers |

FOREIGN PATENT DOCUMENTS

| | | |
|---|---|---|
| GB | 701633 | 12/1953 |
| GB | 714160 | 8/1954 |
| LU | 60116 | 12/1969 |
| NL | 18441 | 8/1928 |
| WO | WO 86/04603 | 8/1986 |
| WO | WO 94/12596 | 6/1994 |
| WO | WO 96/41852 | 12/1996 |

OTHER PUBLICATIONS

Patent Abstract of Japan, vol. 1997, No. 10 Oct. 31, 1997, JP 09 154504 (Asahi Denka Kogyo KK), Jun. 17, 1997.

Erickson, David R., *Degumming and Lecithin and Utilization*, in Practical Handbook of Soybean Processing and Utilization 174, 179–80 (David R. Erickson ed. 1995).

J. C. Schmidt and F.T. Orthoefer, *Modified Lecithins*, in Lecithins 203, 206 (Bernard F. Szuhaj & Gary R. List eds., 1985).

Van Nieuwenhuyzen, W., Lecithin Production and Properties, *J. Amer. Oil Chem. Soc.* 53:425 (1976).

*Primary Examiner*—Deborah D. Carr
(74) *Attorney, Agent, or Firm*—McDonnell Boehnen Hulbert & Berghoff

(57) ABSTRACT

This invention relates to improved methods for treating phosphatide-containing mixtures. More particularly, this invention relates to methods for recovering purified vegetable oil, aqueous organic acid, and organic acid-treated phosphatide from a phosphatide-containing mixture comprising an acid-and-oil mixture obtained from organic acid refining of vegetable oil.

15 Claims, 2 Drawing Sheets

METHODS FOR TREATING PHOSPHATIDE-CONTAINING MIXTURES

CROSS-REFERENCE

This application is a continuation-in-part of U.S. patent application Ser. No. 09/550,375, filed Apr. 14, 2000, now abandoned which is a divisional of U.S. patent application Ser. No. 09/197,953, filed Nov. 20, 1998, now U.S. Pat. No. 6,172,248.

FIELD OF THE INVENTION

This invention relates to improved methods for treating phosphatide-containing mixtures. More particularly, this invention relates to methods for recovering purified vegetable oil, aqueous organic acid, and organic acid-treated phosphatide from a phosphatide-containing mixture comprising an acid-and-oil mixture obtained from organic acid refining of vegetable oil.

BACKGROUND OF THE INVENTION

Vegetable oils are typically obtained by pressing or extracting the oil seeds of plants such as corn or soybeans. Properly processed vegetable oils are suitable for use in many edible oil and fat compositions destined for human consumption. Such edible oils and fats include salad oils, cooking oils, frying fats, baking shortenings, and margerines. In addition to being widely used in edible oils and fats, vegetable oils are also increasingly utilized in important industrial products such as caulking compounds, disinfectants, fungicides, printing inks, and plasticizers.

Vegetable oils primarily consist of triglycerides, also termed triacylglycerols. In addition to triglycerides, however, vegetable oils also contain several other compounds. Some of these additional compounds, such as mono- and di-glycerides, tocopherols, sterols, and sterol esters, need not necessarily be removed during processing. Other compounds and impurities such as phosphatides, free fatty acids, odiferous volatiles, colorants, waxes, and metal compounds negatively affect taste, smell, appearance and storage stability of the refined oil, and hence must be removed. Carefully separated, however, some of these additional compounds, particularly the phosphatides, are valuable raw materials. It is therefore important to select a vegetable oil purifying method that maximizes removal of impurities but does so in a way that least impacts the compounds removed.

Vegetable oil triglycerides are esters of 1,2,3-propane triol, and can be represented by the generic formula

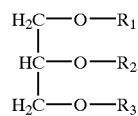

where $R_1$, $R_2$, and $R_3$ are the same or different, and are selected from the group consisting of $C_{10}$–$C_{22}$ saturated and unsaturated fatty acids. In soybean oil in particular, the saturated fatty acids that can occur include but are not limited to lauric (C12:0), myristic (C14:0), palmitic (C16:0), stearic (C18:0), arachidic (C20:0), and behenic (C22:0) acids. Generally, however, the fatty acids of soybean oil are predominantly unsaturated, and include but are not limited to oleic (C18:1), linoleic (C18:2), and linolenic (C18:3) acids. Unsaturated fatty acids can exist as geometric and/or positional isomers, each such isomer having different properties such as melting point. Naturally occurring fatty acids generally exist in the cis form, but they can be converted into the trans form during the course of purification steps used to produce a vegetable oil from an oilseed. Crude soybean oil in particular typically contains from about 95 to about 97 percent by weight triglycerides.

The terms phosphatides and phosphatide concentrates are commonly used to refer to a mixture of phospholipids comprising phosphatidyl derivatives which are present in crude vegetable oil. Phosphatides are also called gums, wet gums, lecithin, and wet lecithin. The term lecithin, from a true chemical sense, refers to phosphatidyl choline. However, as used by commercial suppliers, the term lecithin refers to a product derived from vegetable oils, especially soybean oil. Specific chemical components of phosphatides present in vegetable oil include phosphatidyl choline, 1; phosphatidylethanolamine, 2; phosphatidylinositol, 3; phosphatidyl serine, 4; phosphatidic acid, 5; cyclolipids, and other components such as free sugars, metals and free fatty acids.

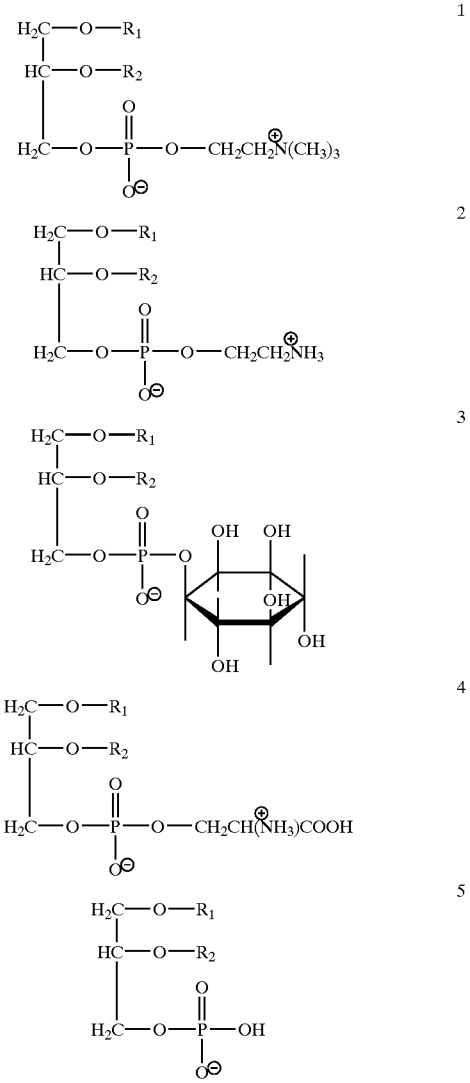

Such phosphatides are amphipathic, i.e., one end of the molecule is hydrophilic (lipophobic) and the other end is hydrophobic (lipophilic). As a result, they possess useful surface-active properties, and can orient in aqueous environments to create membranes and bilayers.

The fatty acid content of the phosphatides 1 through 5 is represented by $R_1$ and $R_2$, as defined above, and generally matches that of the vegetable oil from which they are derived. The phosphatide content of vegetable oil will vary based on a number of factors, including but not limited to oilseed type, seed quality, and the process by which oil is extracted therefrom. Crude soybean oil in particular typically contains from about 1.5 to about 3 percent by weight phosphatides. Phosphatides comprise both hydratable phosphatides (HPs) and non-hydratable phosphatides (NHPs). Although non-hydratable phosphatides tend to remain oil-soluble and are largely unaffected by water, hydratable phosphatides when hydrated become greater in density than the triglycerides and precipitate, or settle out. This phenomenon forms the basis for the process of conventional water degumming, discussed more fully below.

Vegetable oil impurities are typically removed in four distinct steps of degumming, refining, bleaching, and deodorizing. Of these four steps, degumming removes the largest amount of impurities, the bulk of which are hydratable phosphatides. Refining primarily removes non-hydratable phosphatides, soaps created from the neutralization of free fatty acids, and other impurities such as metals. Bleaching then improves the color and flavor of refined oil by decomposing peroxides and removing oxidation products, trace phosphatides, and trace soaps. Soybean oil bleaching materials include neutral earth (commonly termed natural clay or fuller's earth), acid-activated earth, activated carbon, and silicates. Deodorizing is the final processing step and prepares the oil for use as an ingredient in many edible products including salad oils, cooking oils, frying fats, baking shortenings, and margerines. The deodorizing process generally comprises passing steam through refined oil at high temperature and under near vacuum conditions to vaporize and carry away objectionable volatile components.

Vegetable oil refining, also known as neutralization or deacidification, essentially involves removing free fatty acids (FFA) and phosphatides from the vegetable oil. Most refining operations employ either alkali refining (also termed caustic refining) or physical refining (also termed steam refining). Of these two refining methods, alkali refining predominates.

For either refining method, an optional but preferred first step is a conventional water degumming process. Degumming refers to the process of removing hydratable phosphatides and other impurities such as metals from vegetable oils. A simple degumming process comprises admixing soft water with the vegetable oil and separating the resulting mixture into an oil component and an oil-insoluble hydrated phosphatides component (frequently referred to as a "wet gum" or "wet lecithin"). The NHPs, generally considered to be calcium and magnesium salts of phosphatidic acids, are largely unaffected by water and remain soluble in the oil component. Phosphatidic acids are typically produced via the action of phospholipidase D, which splits off the non-fatty-acid moiety from phospholipids.

Normally, refiners also must introduce chelating agents following degumming processes to remove metal compounds from crude vegetable oil, which typically contains calcium, potassium, magnesium, aluminum, iron and copper. Left in place, these metal impurities form salts of phosphatidic acid, thereby contributing to the NHP content. Moreover, metal contaminants, especially iron, can darken oil during deodorization, and even small amounts of iron that do not affect the oil's color can nevertheless dramatically reduce stability of refined oil.

Treating crude vegetable oil with soft water produces a degummed oil and a phosphatide concentrate containing the hydratable phosphatide fraction. This phosphatide concentrate subsequently can be removed from the degummed oil by a convenient method such as by gravitational force or by centrifugal separation. Phosphatide concentrates coming from centrifugal separation will generally contain up to about fifty percent by weight water, and typically will contain from about twenty-five to about thirty percent by weight water. In order to minimize chances of microbial contamination, phosphatide concentrates must be dried or otherwise treated immediately. Dried phosphatide concentrates can be profitably sold as commercial lecithin. Degummed oil is further refined to remove NHPs and other unwanted compounds.

Mineral acid also is sometimes added during the water degumming process to help minimize the NHP content of degummed oil. The acid combines with calcium and magnesium salts, enabling phosphatidic acids to migrate from the oil to the water phase, thus eliminating them from the crude oil. However, using mineral acid during degumming is inappropriate when seeking to recover gums intended for use as lecithin because the presence of mineral acid will cause darkening of the lecithin.

In alkali refining, free fatty acids and gums are removed from crude or degummed oil by mixing the oil with a hot, aqueous alkali solution, producing a mixture of so-called neutral oil and soapstock (also termed refining byproduct lipid), which is an alkaline mixture of saponified free fatty acids and gums. The neutral oil is then separated from the soapstock, typically by centrifugation. The soapstock has commerical value due to its fatty acid content but must be processed further in order to render it salable. The neutral oil is further processed to remove residual soap.

Soapstock is treated in a process called acidulation, which involves breaking or splitting the soap into separate oil and aqueous phases through addition of a mineral acid such as sulfuric acid to reduce the pH to approximately 1.5, followed by thorough heating and mixing. Because the aqueous phase is heavier than the oil phase, the acidulated soapstock is separated from the oil by gravity or centrifugation. The separated oil (termed acid oil) has essentially the composition of the neutral oil and is drawn off, washed with water to completely remove mineral acid and sludge, and sold, usually as an animal feed supplement. The remaining aqueous phase (termed acid water) is the final waste product and must be neutralized before being discarded.

The alkali refining process has several drawbacks, however. One drawback is that alkali refining requires large amounts of high-quality water and creates a correspondingly high amount of wastewater that creates expensive and troublesome disposal concerns. For example, in preparing the aqueous alkali and aqueous mineral acid solutions used in alkali refining, the required water must be demineralized to prevent conversion of HPs into NHPs. In separating neutral oil from soapstock, centrifugation alone is insufficient to completely remove soapstock, and thus a demineralized water wash at a rate of about 10 to 12 percent by weight of the feed is required to aid separation of soapstock. In acidulating the soapstock, which by this time comprises about 50 percent by weight water, aqueous mineral acid must be used in considerable excess, thereby contributing even more water. A typical alkali refining operation requires a demineralized water usage rate of about 0.1 times the amount of oil being treated.

Having then incurred the cost of using large amounts of high-quality water, alkali refiners essentially throw that water investment away in the form of an acid water waste stream, disposal of which is even then only possible after having incurred further additional costs relating to pollution control. The acid water created during soapstock splitting is high in biochemical oxygen demand (BOD) and low in pH. Disposal regulations require at minimum that the acid water be neutralized before the waste can be dumped. Many states have much more stringent pollution controls, requiring often costly solutions to ensure effluent biodegradability.

Another drawback is refining losses that occur due to the soapstock's emulsifying effect, wherein soapstock acts to take up a portion of the valuable neutral oil into the aqueous soapstock solution. To minimize such emulsification losses, the crude or degummed oil is usually heated to between 158° F. and 194° F. prior to being contacted with the hot alkali solution. However, heating will not completely prevent emulsions from forming, nor will it entirely break emulsions once formed. Centrifugation forces also are insufficient to completely break emulsions of neutral oil in soapstock.

An additional drawback to alkali refining is losses that occur when a portion of the neutral oil undergoes alkaline hydrolysis, often referred to as saponification, to produce undesirable fatty acid salts. Allowing the alkali solution and the crude or degummed oil to remain in contact for only short times can minimize saponification losses but is often insufficient to remove impurities other than fatty acids, especially impurities such as phosphatides and metal compounds. Consequently, short contact times can make it necessary to conduct a second round of refining.

Yet another alkali refining drawback is that raw soapstock is troublesome to handle. Soapstock solidifies quickly upon cooling, so heated holding tanks and transfer lines are required to maintain temperatures above 140° F. Elevated temperatures also are required to prevent fermentation. On the other hand, overly heating soapstock causes it to boil, producing excessive and troublesome foaming.

Thus, alkali refining involves many processing steps and has many drawbacks. In attempting to address the problems associated with alkali refining, operators must simultaneously vary many factors including the amount of heat applied, the amount and concentration of alkali, and retention times. Successfully balancing all these factors is a complex and difficult task. Furthermore, successful balancing of factors nevertheless can leave the need for additional refining cycles.

An alternative to alkali refining is physical refining. Physical refining is a steam distillation process essentially the same as that used in conventional vegetable oil deodorization processes, in which steam passing through vegetable oil vaporizes and carries away free fatty acids. The main advantage of physical refining over alkali refining is that no soapstock is generated. A second advantage is lower refining losses because there is no saponification of oil and no oil entrainment and/or emulsification by soapstock.

Accordingly, there is significant interest in physical refining due to its economic advantages and friendliness compared to alkali refining. But because physical refining does not remove NHPs, any oils to be physically refined must be free of NHPs in order to ensure stable refined oils. Oils such as palm oil and tallow, which have low NHP content, can be successfully physically refined. But oils such as soybean oil and sunflower seed oil, which are relatively high in NHPs, are not commonly physically refined because the pre-refining step of water degumming does not remove NHPs. Moreover, physically refined soybean oils have only limited acceptance in the U.S. market due to their lack of flavor stability.

Thus, although present methods exist for refining vegetable oils, significant drawbacks remain. Alkali refining can substantially remove phosphatides and other impurities but presents economic challenges and water pollution concerns. Physical refining is economically and environmentally less challenging, but many vegetable oils including soybean oil which are high in NHPs cannot be acceptably physically refined.

Consequently, further improvements in purifying vegetable oil, and especially soybean oil, have been sought, particularly with regard to obtaining purified vegetable oil low in free fatty acids, phosphatides, and other impurities such as metals in an environmentally friendly manner. The present invention relates to an improved process having advantages over those previously disclosed. In particular, this invention relates to improved methods for treating phosphatide-containing mixtures.

SUMMARY OF THE INVENTION

One aspect of the present invention relates to an improved process for treating phosphatide-containing mixtures. An improved process of the present invention effectively recovers purified vegetable oil, aqueous organic acid, and organic acid-treated phosphatide from a phosphatide-containing mixture comprising an acid-and-oil mixture obtained from organic acid refining of vegetable oil.

Another aspect of the invention relates to an improved process for treating phosphatide-containing mixtures that produces an environmentally friendly aqueous organic acid phase that can be recovered and used without subsequent processing, thereby allowing the water used in organic acid refining to be nearly completely recycled.

One embodiment of the invention is a process for treating a phosphatide-containing mixture that comprises the steps of providing a phosphatide-containing mixture obtained from an organic acid refining process; separating the phosphatide-containing mixture into a purified vegetable oil phase and a phosphatide-enriched aqueous phase; and removing the purified vegetable oil phase.

Another embodiment of the invention is a process for treating a phosphatide-containing mixture that comprises the steps of providing a phosphatide-containing mixture obtained from an organic acid refining process; separating the phosphatide-containing mixture into a purified vegetable oil phase and a phosphatide-enriched aqueous phase; removing the purified vegetable oil phase; separating the phosphatide-enriched aqueous phase into an aqueous organic acid phase and an organic acid-treated phosphatide phase; and removing either the aqueous organic acid phase or the organic acid-treated phosphatide phase.

Yet another embodiment of the invention is a process for treating a phosphatide-containing mixture that comprises the steps of providing a phosphatide-containing mixture obtained from an organic acid refining process; separating the phosphatide-containing mixture into a purified vegetable oil phase and a phosphatide-enriched aqueous phase; removing the purified vegetable oil phase; separating the phosphatide-enriched aqueous phase into an aqueous organic acid phase and an organic acid-treated phosphatide phase; removing either the aqueous organic acid phase or the organic acid-treated phosphatide phase; and recycling the aqueous organic acid phase into the organic acid refining process.

A further embodiment of the invention is a process for treating a phosphatide-containing mixture that comprises the steps of providing a phosphatide-containing mixture obtained from an organic acid refining process; separating the phosphatide-containing mixture into a purified vegetable oil phase, an aqueous organic acid phase, and an organic acid-treated phosphatide phase; and removing the purified vegetable oil phase.

A still further embodiment of the invention is a process for treating a phosphatide-containing mixture that comprises the steps of providing a phosphatide-containing mixture obtained from an organic acid refining process; separating the phosphatide-containing mixture into a purified vegetable oil phase, an aqueous organic acid phase, and an organic acid-treated phosphatide phase; removing the purified vegetable oil phase; and removing either the aqueous organic acid phase or the organic acid-treated phase.

An even further embodiment of the invention is a process for treating a phosphatide-containing mixture that comprises the steps of providing a phosphatide-containing mixture obtained from an organic acid refining process; separating the phosphatide-containing mixture into a purified vegetable oil phase, an aqueous organic acid phase, and an organic acid-treated phosphatide phase; removing the purified vegetable oil phase; removing either the aqueous organic acid phase or the organic acid-treated phase; and recycling the aqueous organic acid phase into the organic acid refining process.

A yet further embodiment embodiment of the invention is a process for treating a phosphatide-containing mixture that comprises the steps of providing a phosphatide-containing mixture obtained from an organic acid refining process; separating the phosphatide-containing mixture into a purified vegetable oil phase, an aqueous organic acid phase, and an organic acid-treated phosphatide phase; removing the aqueous organic acid phase; and recycling the aqueous organic acid phase into the organic acid refining process.

These and other aspects of the invention will become apparent in light of the detailed description below.

DESCRIPTION OF A PREFERRED EMBODIMENT

Figure 1:
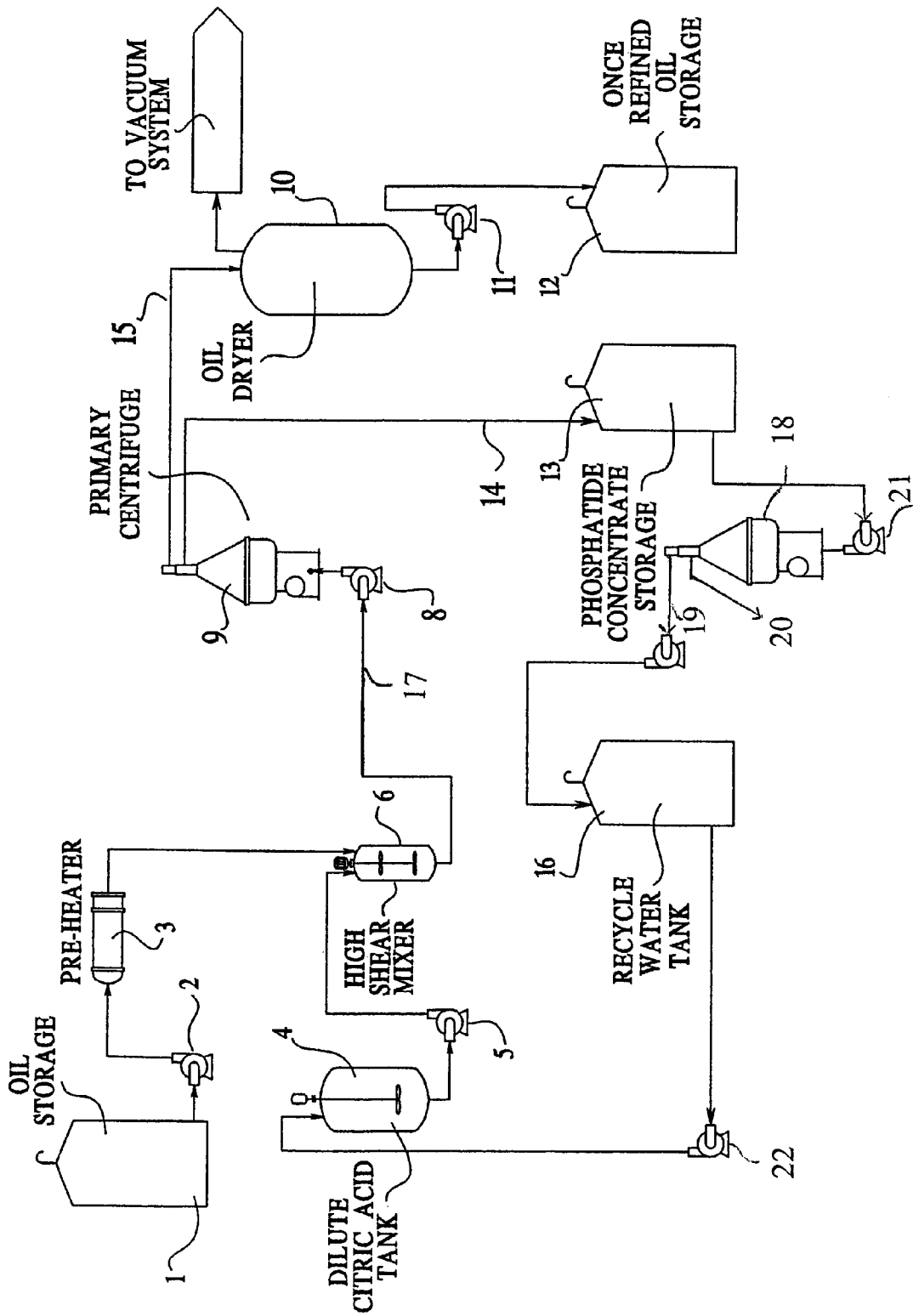
FIG. 1 is a process flow scheme suitable for carrying out one embodiment of the invention.
Figure 2:
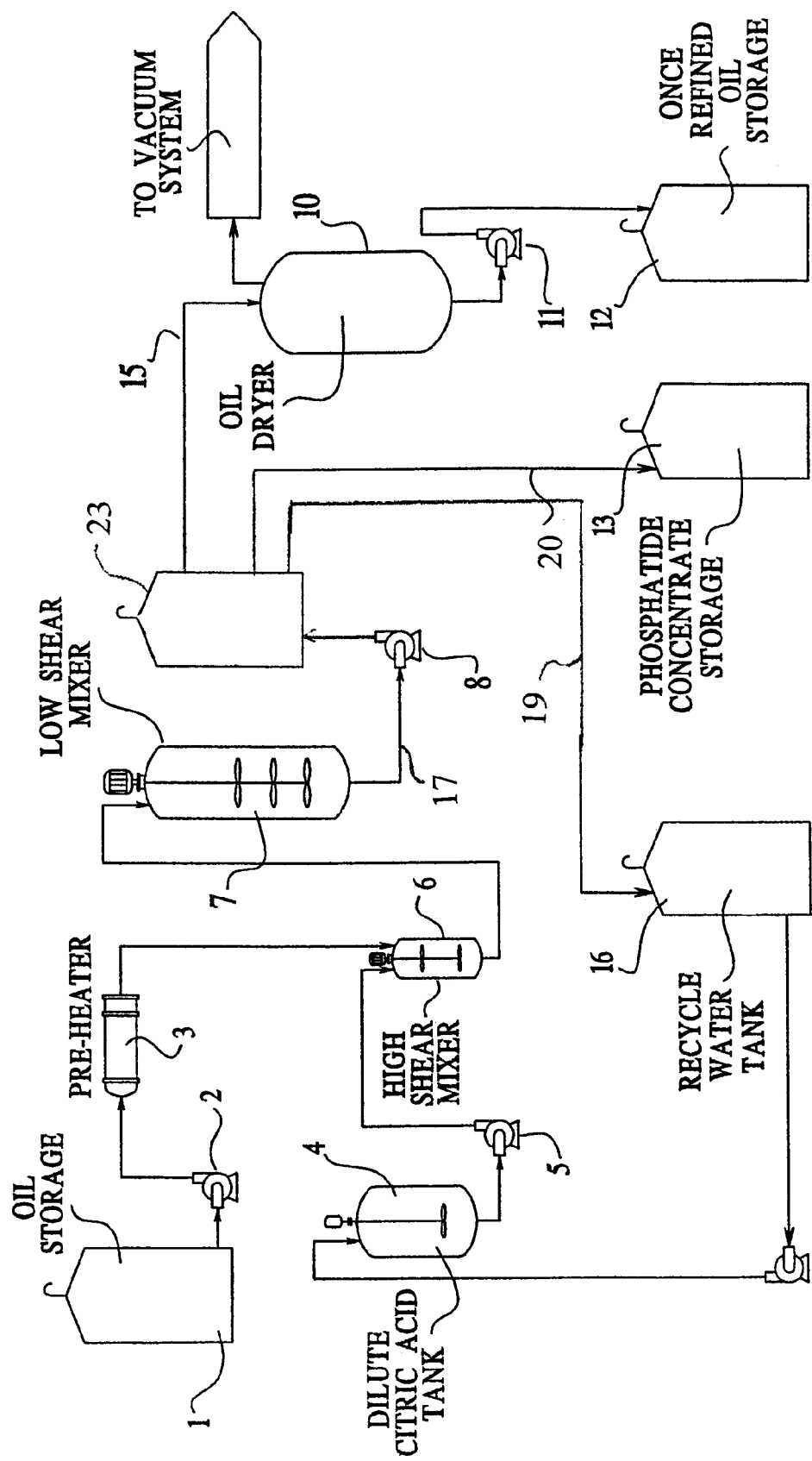
FIG. 2 is a process flow scheme suitable for carrying out another embodiment of the invention.

Phosphatide-containing mixtures can be obtained from organic acid refining of vegetable oil, as disclosed in pending U.S. patent application Ser. No. 09/550,375 and U.S. patent application No. 09/197,953, herein incorporated by reference in their entirety. The improved processes of the invention for treating a phosphatide-containing mixture can be conducted as batch or continuous processes. As illustrated in FIG. 1 and FIG. 2, in an organic acid refining process, crude or degummed vegetable oil is supplied from a storage tank 1 through pump 2 to a pre-heater 3 wherein the vegetable oil is heated to a temperature of from about 190° F. to about 220° F. Suitable vegetable oils include but are not limited to those derived from soybean oil, corn oil, cottonseed oil, palm oil, peanut oil, rapeseed oil, safflower oil, sunflower seed oil, sesame seed oil, rice bran oil, coconut oil, canola oil, and mixtures thereof. A particularly preferred vegetable oil is soybean oil.

The vegetable oil to be purified can be either crude or "degummed" oil. Degumming refers to the process of removing hydratable phosphatides from crude vegetable oils during refining. Crude vegetable oil contains both hydratable and non-hydratable phosphatides. A simple degumming process comprises admixing water with the vegetable oil and separating the resulting mixture into an oil component and an oil-insoluble hydrated phosphatides component (frequently referred to as a "wet gum" or "wet lecithin"). Non-hydratable phosphatides, generally considered to be calcium and magnesium salts of phosphatidic acids, are largely unaffected by water and remain soluble in the oil component. Treating crude vegetable oil with water thus produces a phosphatide concentrate containing the hydratable phosphatide fraction and a degummed oil containing the non-hydratable phosphatide fraction. This degummed oil can be removed from the phosphatide concentrate by a convenient method such as centrifugal separation.

The crude or degummed vegetable oil is heated in pre-heater 3 to a temperature of from about 190° F. to about 220° F., preferably from about 195° F. to about 215° F., and most preferably from about 200° F. to about 210° F., depending on the source from which the vegetable oil was derived. Heating the vegetable oil minimizes the potential for losses due to emulsification when the oil is later contacted with an aqueous phase. Heating the vegetable oil also produces preferred handling viscosities and facilitates later mixing steps. Pre-heater 3 can be constructed according to many designs and can impart heat directly or indirectly to the vegetable oil. A preferred pre-heater 3 is a shell and tube heat exchanger available from Doyle & Roth and having an overall heat transfer coefficient of 170 BTU/h/ft$^2$/° F.

The heated vegetable oil is introduced into high shear mixer 6 wherein it is combined with a dilute aqueous organic acid solution supplied from a source 4 via pump 5, thereby producing an acid-oil blend. When organic acid refining is carried out as a batch process, the heated vegetable oil and the dilute aqueous organic acid solution can be introduced sequentially or simultaneously and in any order into high shear mixer 6. When organic acid refining is carried out as a continuous process, the heated vegetable oil and the dilute aqueous organic acid solution are introduced simultaneously into high shear mixer 6. The dilute aqueous organic acid solution optionally can be heated prior to its addition into high shear mixer 6.

The dilute aqueous organic acid solution may be prepared from any food grade organic acid, including but not limited to phosphoric acid, acetic acid, citric acid, tartaric acid, succinic acid, or combinations thereof. A particularly preferred organic acid is citric acid. Using a food grade organic acid, as opposed to a mineral acid, ensures that phosphatides removed during the purifying process can be purified and sold as commercial lecithin to the food industry. Using an organic acid also enables sequestering metal contaminants without the need to add other chelating agents.

The dilute aqueous organic acid solution can be prepared by dissolving an appropriate amount of a solid organic acid in water, or it can be prepared by further diluting a previously prepared aqueous organic acid solution of greater strength. In preparing the dilute aqueous organic acid solution, demineralized water is preferably used. Using demineralized water avoids the possibility of converting hydratable phosphatides to non-hydratable phosphatides. As used herein, the term demineralized water means water substantially devoid of calcium and magnesium ions.

The dilute aqueous organic acid solution has a concentration based on the combined weight of organic acid and water of from about 1 to about 5 percent by weight, preferably from about 2 to about 4 percent by weight, and most preferably from about 2 to about 3.5 percent by weight. The dilute aqueous organic solution is combined with the heated vegetable oil in a ratio of from about 3:97 to about 20:80, preferably from about 5:95 to about 17:83, and most preferably from about 8:92 to about 15:85, depending on the source from which the vegetable oil is derived and on whether the vegetable oil has been degummed.

The acid-oil blend is mixed at high shear in the high shear mixer 6 for a time sufficient to finely disperse the dilute aqueous organic acid solution in the vegetable oil and provide a phosphatide-containing mixture 17 (also termed an acid-and-oil mixture). Generally, the acid-oil blend is mixed for a time of less than about 120 seconds, preferably less than about 100 seconds, and most preferably less than about 60 seconds. Mixing parameters are selected according to the mechanical design of the high shear mixer. Important mixer design criteria include the ratio of tank height to tank diameter, the ratio of impeller diameter to tank diameter, and the number and positioning of individual blades on the impeller. A preferred high shear mixer 6 is a High Shear Mixer MX100 available from Alfa Laval and having a tank height to tank diameter ratio of about 4:1. Preferably, high shear mixer 6 employs 5 impellers, 2 of which are radial flow impellers and 3 of which are axial flow impellers, disposed along a mixing shaft connected to a motor generating from about 30 to about 40 horsepower.

High shear as used herein means mixer design criteria and impeller operating conditions combining to produce flow velocities of at least about 45 feet per second. High shear mixing generally requires at least one impeller rotating at a speed of from about 900 to about 1500 rpm and having a blade tip speed of from about 4000 to about 9000 ft/min, thereby generating high shear flow velocities of at least about 45 feet per second.

The phosphatide-containing mixture generally comprises hydratable phosphatides, nonhydratable phosphatides that have been converted into hydratable phosphatides, water, organic acid, and vegetable oil, as well as other contaminants including but not limited to metals. Ideally, the contaminants, especially the metals, are sequestered into the phosphatide-enriched aqueous phase (also termed a hydrated impurities phase). The term sequestering as used herein refers to the process wherein contaminants are either directly or indirectly (through chemical conversion into water-soluble forms) taken up into the phosphatide-enriched aqueous phase.

With reference to FIG. 1, in one embodiment of the invention the phosphatide-containing mixture 17, which comprises the combined purified vegetable oil and phosphatide-enriched aqueous phases, is advantageously pumped to a centrifuge 9 via pump 8, wherein the two phases undergo centrifugal separation and exit as separate physical streams 14 (comprising the phosphatide-enriched aqueous phase) and 15 (comprising the purified vegetable oil phase). The purified vegetable oil phase 15 can be further processed, as for example by bleaching and deodorizing, and subsequently use d or sold.

Suitable centrifuges as referenced in this application include but are not limited to disc-bowl units that are self-cleaning and capable of production rates of up to about 700 tons per day. A majority of U.S. refiners utilize hermetic-type centrifuges, which allow control of the separation zone by adjusting back-pressure. A preferred centrifuge 9 is a PX 90 self-cleaning unit available from Alfa Laval.

Alternatively, the phosphatide containing mixture 17 can be sent to a holding vessel and allowed to remain unagitated for a time sufficient to develop a purified vegetable oil phase 15 and a phosphatide-enriched aqueous phase 14. This route can be employed because the purified vegetable oil typically separates fairly quickly from the phosphatide-enriched aqueous phase. Generally, separation into discrete phases begins to occur within about 0.5 hours, with complete separation of purified vegetable oil occurring within about 24 hours. Once a discrete purified vegetable oil phase 15 is formed, it can be separated from the phosphatide-enriched aqueous phase 14 via any convenient method. Advantageously, the purified vegetable oil phase 15 formed by this route is decanted away from the phosphatide-enriched aqueous phase 14.

The phosphatide-enriched aqueous phase 14 comprises an aqueous organic acid phase and an organic acid-treated phosphatide phase. The phosphatide-enriched aqueous phase 14 can undergo immediate further processing or it can be sent to a holding vessel. If the phosphatide-enriched aqueous phase 14 is sent to a holding vessel and stored for any appreciable amount of time, precautions which are well known to those of skill in the art must be taken to minimize the chance of microbial contamination.

Advantageously, the phosphatide-enriched aqueous phase 14 is sent to holding vessel 13, and thereafter pumped to a centrifuge 18 via pump 21, wherein it undergoes centrifugal separation and exits in separate physical streams 19 (comprising an aqueous organic acid phase) and 20 (comprising an organic acid-treated phosphatide phase). As discussed above, many centrifuges are suitable for this type of operation. One preferred centrifuge 18 is a PX 90 self-cleaning unit available from Alfa Laval.

Alternatively, the phosphatide-enriched aqueous phase 14 is sent to holding vessel 13 and allowed to remain unagitated for a time sufficient to develop an aqueous organic acid phase 19 and an organic acid-treated phosphatide phase 20. Generally, separation into discrete phases begins to occur within about 0.5 hours, with complete separation of aqueous organic acid occurring within about 24 hours. As discussed above, if this route is selected, precautions must be taken to minimize the risk of microbial contamination. Once a discrete aqueous organic acid phase 19 is formed, it can be separated from the organic acid-treated phosphatide phase 20 via any convenient method. The organic acid-treated phosphatide phase 20 can be processed further thereafter.

The aqueous organic acid phase 19 can be recycled without further treatment into the organic acid refining process. Advantageously, aqueous organic acid phase 19 is pumped into the dilute aqueous organic acid solution source 4 via pump 22. Alternatively, aqueous organic acid phase 19 can be sent to holding vessel 16 prior to pumping into the dilute aqueous organic acid solution source 4. Because the aqueous organic acid phase 19 can be directly recycled and need not be disposed, processes of the invention employing recycle are economically more efficient than conventional refining methods, such as alkali refining, because process water is not thrown away as wastewater, and because there is no need for time-consuming, troublesome, and expensive wastewater remediation. Refining operations employing organic acid refining with recycle of the aqueous organic acid phase generate substantially no discharge water and require an overall demineralized water usage rate of only about 0.00081 times the amount of oil being treated. Essentially, the only water that is not ultimately recovered in practicing processes of the invention is water that remains in the organic acid treated phosphatide 20 and water that remains as moisture in the purified vegetable oil phase 15. This minimal water loss is dramatically less than conventional refining operations, which as discussed above typically require a demineralized water usage rate of about 0.1 times the amount of oil being treated. This minimal water loss also can allow a vegetable oil refining operation to be much more environmentally friendly than conventional refining operations. Indeed, it is often the case in certain areas, such as Europe, that water use and disposal is a deciding factor in determining whether to allow a refinery to be built or even continue to exist in a particular location.

With reference to FIG. 2, in another embodiment of the invention the phosphatide-containing mixture 17 is advantageously pumped to a holding vessel 23 via pump 8 and allowed to remain unagitated for a time sufficient to develop a purified vegetable oil phase 15, an organic acid-treated phosphatide phase 20, and an aqueous organic acid phase 19. Generally, separation into discrete phases begins to occur within about 0.5 hours, with complete separation of phases occurring within about 24 hours. Typically, the purified vegetable oil phase 15 migrates to the top, the organic acid-treated phosphatide phase 20 migrates to the middle, and the aqueous organic acid phase 19 migrates to the bottom. Once discrete phases exist, they can be separated from each other in any order. Typically, however, the purified vegetable oil phase 15 is separated first, and then one of the two remaining phases is then separated from the other. Purified vegetable oil phase 15 can be separated via any convenient method, although preferably it is decanted away from the other two phases.

The purified vegetable oil phase 15 can be further processed, as for example by bleaching and deodorizing, and subsequently used or sold. The organic acid-treated phosphatide phase also can be further processed, either immediately or after having been sent to and stored in holding vessel 13, adequate precautions having been taken against the risk of microbial contamination. And as in the embodiment depicted in FIG. 1, the aqueous organic acid phase 19 can be recycled without further treatment, either immediately or after having been sent to a holding vessel 16, into the organic acid refining process.

All documents, e.g., patents, journal articles, and textbooks, cited above or below are hereby incorporated by reference in their entirety.

One skilled in the art will recognize that modifications may be made in the present invention without deviating from the spirit or scope of the invention. The invention is illustrated further by the following examples, which are not to be construed as limiting the invention in spirit or scope to the specific procedures or compositions described therein.

EXAMPLE 1

An aqueous citric acid solution containing 3 percent by weight citric acid based on the combined weight of citric acid and water was admixed with crude filtered soybean oil in a ratio of 10:90. The resulting acid-oil blend was mixed in a high shear mixer for 30 seconds to give a phosphatide-containing mixture, which was then centifuged to separate a purified soybean oil phase a phosphatide-enriched aqueous phase. The resultant purified soybean oil had the characteristics shown in Table I. The phosphatide-enriched aqueous phase was then allowed to remain unagitated for 24 hours to produce an aqueous citric acid phase and a citric acid-treated phosphatide phase. The aqueous citric acid phase was then withdrawn and recycled into the citric acid solution used in the organic acid refining process. The citric acid-treated phosphatide was subsequently dried.

TABLE I

|  | Organic Acid Refined Soybean Oil of Example 1 ppm | Conventional Water-Degummed Soybean Oil ppm |
| --- | --- | --- |
| Iron | <0.1 | 1.0 |
| Magnesium | <5 | 50 |
| Calcium | <5 | 80 |
| Phosphorous | <10 | 150 |

EXAMPLE 2

An aqueous citric acid solution containing 3 percent by weight citric acid based on the combined weight of citric acid and water was admixed with crude filtered soybean oil in a ratio of 10:90. The resulting acid-oil blend was mixed in a high shear mixer for 30 seconds to give a phosphatide-containing mixture. The phosphatide-containing mixture was then transferred to a holding tank and allowed to remain unagitated for 24 hours to produce a purified soybean oil phase, a citric acid-treated phosphatide phase, and an aqueous citric acid phase, oriented in order from top to bottom. The purified soybean oil phase was decanted away, and the aqueous citric acid phase then was withdrawn and recycled into the citric acid solution used in the organic acid refining process. The citric acid-treated phosphatide was subsequently dried.

The invention and the manner and process of making and using it, are now described in such full, clear, concise and exact terms as to enable any person skilled in the art to which it pertains, to make and use the same. Although the foregoing describes preferred embodiments of the present invention, modifications may be made therein without departing from the spirit or scope of the present invention as set forth in the claims. To particularly point out and distinctly claim the subject matter regarded as invention, the following claims conclude this specification.

What we claim is:

1. A process for treating a phosphatide-containing mixture, comprising:
    (a) providing a phosphatide-containing mixture obtained from an organic acid refining process;
    (b) separating the phosphatide-containing mixture into a purified vegetable oil phase and a phosphatide-enriched aqueous phase; and
    (c) removing the purified vegetable oil phase.

2. The process of claim 1, wherein step (b) separating is by permitting the phosphatide-containing mixture to settle for a time sufficient to develop a purified vegetable oil phase and a phosphatide-enriched aqueous phase.

3. The process of claim 1, wherein step (b) separating is by centrifugation.

4. The process of claim 1, wherein step (c) removing is by decanting.

5. The process of claim 1, further comprising the steps
    (d) separating the phosphatide-enriched aqueous phase into an aqueous organic acid phase and an organic acid-treated phosphatide phase; and
    (e) removing either the aqueous organic acid phase or the organic acid-treated phosphatide phase.

6. The process of claim 5, wherein step (d) separating is by permitting the phosphatide-enriched aqueous phase to settle for a time sufficient to develop an aqueous organic acid phase and an organic acid-treated phosphatide phase.

7. The process of claim 5, wherein step (d) separating is by centrifugation.

8. The process of claim 5, further comprising step (f) recycling the aqueous organic acid phase into the organic acid refining process.

9. A process for treating a phosphatide-containing mixture, comprising:
   (a) providing a phosphatide-containing mixture obtained from an organic acid refining process;
   (b) separating the phosphatide-containing mixture into a purified vegetable oil phase, an aqueous organic acid phase, and an organic acid-treated phosphatide phase; and
   (c) removing the purified vegetable oil phase.

10. The process of claim 9, wherein step (b) separating is by permitting the phosphatide-containing mixture to settle for a time sufficient to develop a purified vegetable oil phase, an aqueous organic acid phase, and an organic acid-treated phosphatide phase.

11. The process of claim 9, wherein step (b) separating is by centrifugation.

12. The process of claim 9, wherein step (c) removing is by decanting.

13. The process of claim 9, further comprising step (d) removing either the aqueous organic acid phase or the organic acid-treated phosphatide phase.

14. The process of claim 13, further comprising step (e) recycling the aqueous organic acid phase into the organic acid refining process.

15. A process for treating a phosphatide-containing mixture, comprising:
   (a) providing a phosphatide-containing mixture obtained from an organic acid refining process;
   (b) separating the phosphatide-containing mixture into a purified vegetable oil phase, an aqueous organic acid phase, and an organic acid-treated phosphatide phase;
   (c) removing the aqueous organic acid phase; and
   (d) recycling the aqueous organic acid phase into the organic acid refining process.

* * * * *